(12) United States Patent  
Griffin, III et al.

(10) Patent No.: US 6,173,205 B1
(45) Date of Patent: Jan. 9, 2001

(54) ELECTROPHYSIOLOGY CATHETER

(75) Inventors: Joseph C. Griffin, III, Atco; David A. Jenkins, Flanders, both of NJ (US)

(73) Assignee: ProCath Corporation, West Berlin, NJ (US)

( * ) Notice: Under 35 U.S.C. 154(b), the term of this patent shall be extended for 0 days.

(21) Appl. No.: 09/318,026

(22) Filed: May 25, 1999

Related U.S. Application Data

(60) Division of application No. 09/081,501, filed on May 20, 1998, now Pat. No. 5,931,863, which is a continuation-in-part of application No. 08/995,617, filed on Dec. 22, 1997, now abandoned.

(51) Int. Cl.$^7$ ........................................................ A61N 1/05
(52) U.S. Cl. ............................................. 607/122; 607/115
(58) Field of Search ...................................... 607/122, 115, 607/116, 119, 129; 600/374, 372, 373, 375, 393

(56) References Cited

U.S. PATENT DOCUMENTS

| | | | |
|---|---|---|---|
| 4,708,145 | 11/1987 | Tacker, Jr. et al. | 128/419 |
| 4,972,846 | 11/1990 | Owens et al. | 128/784 |
| 5,311,873 | 5/1994 | Savard et al. | 128/696 |
| 5,405,375 | 4/1995 | Ayers et al. | 607/122 |

*Primary Examiner*—Kennedy Schaetzle
(74) *Attorney, Agent, or Firm*—Norman E. Lehrer

(57) ABSTRACT

A defibrillation electrophysiology catheter for stimulating the heart and sensing the resulting activity of the heart for determining a patient's potential to have an arrhythmia occur under uncontrolled circumstances and for defibrillating the heart if fibrillation occurs accidentally during the testing is disclosed. The catheter is provided with electrodes formed on the distal surface of the catheter which is placed near the patient's heart. The electrodes may be placed on the catheter in a variety of configurations. An external electrode in the form of a patch or pad is placed on the patient's back. Energy is applied to the system in order to shock the heart and defibrillate the same. The procedure is less invasive than the procedures requiring the electrodes to be implanted at or near the patient's heart and chest wall and requires less energy and time than the procedures requiring the use of two external paddles.

7 Claims, 3 Drawing Sheets

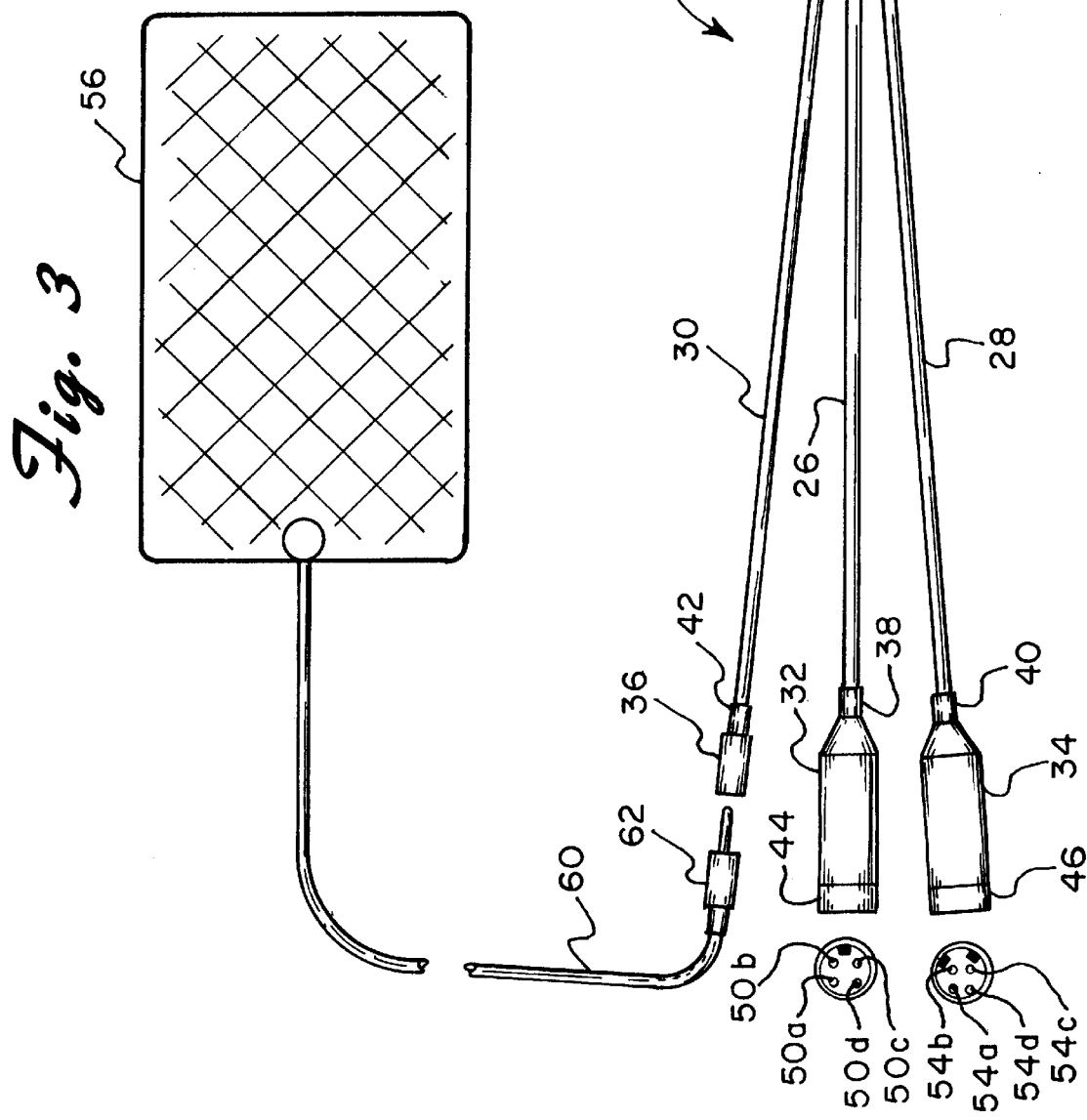

ELECTROPHYSIOLOGY CATHETER

CROSS REFERENCE TO RELATED APPLICATIONS

This application is a division of prior U.S. application Ser. No. 09/081,501 filed May 20, 1998, now U.S. Pat. No. 5,931,863, which is a continuation-in-part of prior U.S. application Ser. No. 08/995,617 filed Dec. 22, 1997, now abandoned.

BACKGROUND OF THE INVENTION

The present invention is directed toward an electrophysiology catheter for studying a patient's heart by stimulating the heart and sensing the resulting activity in order to determine the patient's potential to have an arrhythmia occur under uncontrolled circumstances, and more particularly, toward a defibrillation catheter which may be used to defibrillate the heart if, during the electrophysiology studies, the patient's heart starts to fibrillate.

As is well known in the art, catheters are frequently used with electrodes on the surface thereof for selectively stimulating and/or sensing electrical activity in the body, particularly within the heart. Various electrophysiology studies, such as cardiac mapping and pacing, are conducted using a catheter in order to determine abnormalities in the heart. Generally, a plurality of closely spaced electrodes are placed at the distal end of the catheter where each electrode is coupled to its own connector and is ultimately connected to recording equipment at the proximal end of the catheter. The electrodes sense electrical activity of the heart at localized locations and the resulting activity is recorded.

Electrical energy may also be applied to the electrodes in order to pace the heart. As a result, ventricular tachyarrhythmia may be purposefully induced, or the more lethal ventricular fibrillation may be accidentally induced in the heart. Ventricular fibrillation is an uncoordinated contraction and relaxation of the individual fibers of the heart which produces no blood flow and results in death unless the heart is defibrillated immediately. In order to defibrillate the heart, the electrophysiology catheter must be removed and the patient sedated in order to shock the heart. Typically, a pair of electrodes or paddles are placed across the chest of a patient. Sufficient voltage, i.e., high intensity energy, of, for example 300 to 360 Joules is then applied to depolarize most of the ventricular cells.

This procedure has several disadvantages. For one, the testing must be interrupted in order to defibrillate the heart. The catheter being used for the studies may have to be removed before the electric shock can be applied to the patient. The high intensity of the energy delivered to the patient is traumatic to the patient and may burn the patient's skin. Also, the patient will require a period of recuperation before the testing may continue. As a result, the testing will be delayed and the results may be inaccurate because of the interruption. Furthermore, when tachyarrhythmia or fibrillation occurs, corrective measures must begin immediately. Using the external paddles may delay the defibrillation in that the electrophysiology catheter may have to be removed and the paddles put in position. Not only does this delay increase risk to the patient's life, a high level of energy, for example, 300 to 360 Joules may be necessary in order to defibrillate the heart.

U.S. Pat. No. 5,405,375 recognizes these deficiencies and seeks to overcome them. This patent discloses a mapping catheter which may also be used to defibrillate the heart through the atrium if fibrillation occurs during the mapping. The catheter has a first and second set of a plurality of electrodes located on the distal end. The first set of electrodes is coupled to one connector. The connector is attached to an external defibrillating device. A second electrode may be provided by an additional electrode or a chest wall electrode. The problem with this procedure, however, is that it is rather invasive. That is, a second catheter or electrode must be placed within the patient in order to defibrillate the heart, adding trauma to the patient.

SUMMARY OF THE INVENTION

The present invention overcomes the deficiencies of the prior art described above. It is an object of this invention to provide a defibrillation catheter that defibrillates the heart of a patient and senses electrical activity of the heart.

It is another object of the invention to provide a catheter with at least one electrode formed on the surface of the catheter and an external electrode placed on the patient's back.

It is a further object of the invention to provide a catheter with surface electrodes arranged in a helical or corkscrew configuration and an external electrode placed on the patient's back.

In accordance with the illustrative embodiments demonstrating features and advantages of the present invention, there is provided a catheter with electrodes formed on the surface of the catheter, the catheter being placed near the patient's heart and an external electrode in the form of a patch or pad electrically connected to the catheter and placed on the patient's back in order to defibrillate the heart.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 3 is a perspective view of the present invention;

DETAILED DESCRIPTION OF THE PREFERRED EMBODIMENTS

Figure 1:
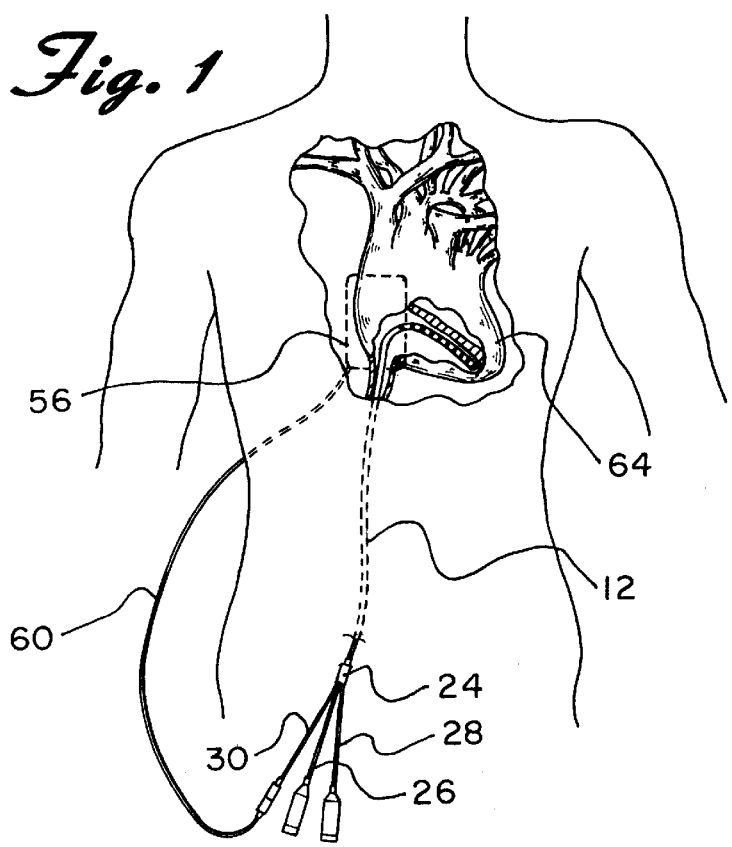
FIG. 1 is a schematic illustration of the present invention placed within a patient.

Referring now to the drawings in detail wherein like reference numerals have been used throughout the various figures to designate like elements, there is shown in FIG. 3 a ventricular defibrillation electrophysiology catheter constructed in accordance with the principles of the present invention and designated generally as 10. Except in those areas which will become clear hereinafter, the ventricular defibrillation electrophysiology catheter 10 is constructed in essentially the same manner as the electrode catheter described in the following co-pending applications: Ser. No. 08/751,436, filed on Nov. 20, 1996 entitled "Temporary Atrial Defibrillation Catheter with Improved Electrode Configuration and Method of Fabrication;" Ser. No. 08/789,937, filed on Jan. 28, 1997, entitled "Focused Energy Array Ablation Catheter;" Ser. No. 08/818,408 filed on Mar. 14, 1997, entitled "Atrial Defibrillation Catheter;" and Ser. No. 08/885,501 filed on Jun. 30, 1997, entitled "Method for Forming an Electrophysiology Catheter." The subject matter of each of these co-pending applications, assigned to the present assignee, is incorporated herein by reference.

The catheter 10 includes an essentially electrically insulative catheter body comprised of an elongated flexible member 12. A preferred material for producing the flexible member is extruded polyether block amide of the type sold by Atochem North America, Inc. under the trademark PEBAX. However, the flexible member 12 may be comprised of other polymeric materials which have excellent memory characteristics such as polyurethane, silicone rubber, and plasticized PVC.

The flexible member 12 has one central lumen (not shown) but it may also have more than one lumen in order to house bare copper wire, to infuse fluids, to sample blood, or to measure pressure. The conductor wire may also be made from stainless steel, platinum, gold, silver, or alloys thereof. The catheter may be of various diameters and sizes in order to accommodate various anatomical or manufacturing conditions. However, the preferred dimensions of the catheter are an outer diameter of 6 French (2 mm) and a length of 115 cm.

The flexible member 12 has a distal end 14 and a proximal end 16. The distal end 14 includes three electrode sections 18, 20, and 22. A manifold 24 is secured around the proximal end 16 of the flexible member 12. Extending outwardly from the manifold 24 are extension tubes 26, 28, and 30. (It should be noted that while these extensions are referred to as tubes, they may also be described as the sheaths of multi-wire cables.) The distal ends of the extension tubes 26, 28, and 30 are connected to the proximal end 16 of the flexible member 12 with potting adhesive, or any other means for securing well known in the art. (See FIG. 3.) The manifold 24 may be several centimeters long and approximately 1 cm in diameter. Connectors 32, 34, and 36 are attached to the proximal ends of the tubes 26, 28, and 30, respectively. The distal ends 38, 40, and 42 of the connectors 32, 34, and 36, respectively, are fixed with adhesive, or any other means for securing well known in the art, to the proximal end of the extension tubes 26, 28, and 30, respectively. The proximal ends 44 and 46 of the connectors 32 and 34, respectively, may be attached to various devices which are used to test or treat the patient as will be further explained below. The electrodes in the electrode sections 18, 20, and 22 are electrically connected to the connectors 32, 34, and 36, respectively, through wires which extend through the lumen of the flexible body 12 and the extension tubes or cables 26, 28, and 30.

Looking at the electrode sections in more detail, the first and most distal electrode section 18 is an electrophysiology section which is used to facilitate intracardiac mapping, sensing, pacing, recording, and stimulation.

In the first section, the preferred electrophysiology electrode arrangement is quadripolar, i.e., there are four separate electrodes 48a–d. However, this is by way of example only and other numbers and arrangements of electrodes could be used as will be discussed below. The individual electrodes range in size from 0.1 to 5 mm. The preferred size is approximately 2 mm. The distance between the electrodes may be between 0.5 to 25 mm. The preferred distance is approximately 5 mm. (The distance is measured from the most proximal edge of one electrode to the most distal edge of an adjacent electrode.) Electrodes 48a–d each may be of any diameter. Preferably, each of the diameters equals the diameter of the flexible member 12. Each of the four electrodes 48a–d is connected to individual copper conductor wires (not shown) that run through the lumen of the catheter body, the electrophysiology stimulator extension tube 26, and connector 32. The wires terminate proximally to four gold-plated contact pins 50a–d which are housed within the connector 32. Although, the wires could also be terminated with insulated contact pins. The first contact pin 50a connects with the most distal electrode 48a. The remaining three pins 50b–d connect to the adjacent electrodes 48b–d, respectively.

The second or middle section 20 is a synchronization electrode, which is used to sense the timing of the "R" wave in the "QRS" complex of the patient's ECG to enable delivery of a defibrillation shock in synchronization with the "R" wave. The second section includes an electrode 52 in a unipolar arrangement. Although a bipolar arrangement may be used. The length of the electrode 52 may be between 0.1 and 10 mm. The preferred length of the electrode 52 is approximately 5 mm. As in the first section of electrodes, it is preferable that the diameter of the electrode 52 equals the diameter of the flexible member 12. The distance between the most proximal electrode, for example, 48d, in the first section and the electrode 52 of the second section is preferably approximately 10 mm. The electrode 52 is connected to a copper conductor wire that runs through the lumen of the catheter body, the companion extension tube 28, and connector 34. The wire terminates proximally to an individual gold plated contact pin 54a housed within the connector 34. There may be more than one pin, for example, 54b–d, however, and the wire could be terminated with a 2 mm insulated contact pin.

The third or proximal section 22 is a defibrillation electrode array which is used as a cathode from which energy is passed through the heart to an interconnected patch or pad electrode 56 which acts as the anode and is positioned on the patient's back during the testing (shown in phantom in FIG. 1). The patch may be rectangular, for example, with a width of 4 inches and a length of 6 inches. However, other sizes and shapes well known in the art may be used. There may be approximately seven electrodes 58a–g in this section and the length of each electrode 58a–g may be approximately 5 mm. As in the first section 18 of electrodes, the distance between electrodes 58a–g in this section is preferably approximately 5 mm. The distance between the electrode 52 of the second section and the most distal electrode, for example, 58a, in the third section is approximately 10 mm. The electrodes 58a–g are connected to conductor wires that run through the lumen of the catheter body, the extension tubing 30, and connector 36 (which may be a female connector). The wires terminate proximally to a contact pin (not shown) housed within female connector 36. The tube 30 is connected to the lead wire 60 of the defibrillation patch electrode 56 via male connector 62 which fits with the female connector 36. (See FIG. 3.)

In order to use the ventricular defibrillation catheter, the distal end 14 of the catheter 10 is inserted into the ventricle 64 of a patient's heart. The electrodes in the first and second sections, 18 and 20, respectively, are connected to various recording devices and energy sources via connectors, 32 and 34 in order to perform various mapping and pacing procedures, as is well known in the art and described above. If during these tests, the patient's heart accidentally goes into fibrillation, energy of up to approximately 50 Joules is applied to the electrodes 58a–g in the third section 22 of the flexible member 12 and to the lead wire 60 of the patch electrode 56. The electrode 52 in the second section 20 is electrically connected to an ECG monitor (not shown). The electrode 52 senses the "R" wave in the "QRS" complex of the patient's ECG and enables the delivery of a defibrillation shock in synchronization with the "R" wave. Once the patient's heart is defibrillated, the tests may resume, without further traumatizing the patient and without requiring any extra time to replace a catheter.

In alternative embodiments of the present invention, a catheter with a number of electrodes, i.e., greater than four, may be used for mapping and pacing a cavity of the heart. In these alternative embodiments the catheter electrode plurality is much greater than a typical quadripolar style. Any number of electrodes such as 8, 10, 64, or greater may be used. The effect of having such a configuration is to provide a catheter not only capable of mapping and/or pacing in the ventricle, but also capable of mapping the entire activation sequence of ventricular tachyarrythmias (VT) in one heart beat (one full cardiac cycle), or even just a few heart beats, combined with cardioversion. Thus, the catheter can induce VT, map VT, and cardiovert the VT rhythm to bring it back to sinus rhythm. That is, rather than having a separate array for delivering the cardioversion energy, the same electrodes may be used for cardioversion as well as mapping and pacing. A means external to the catheter may be used as a relay switch to ensure that all the electrodes act in parallel for delivering the cardioversion energy, but also switches so that all the electrodes act individually for mapping and pacing. The catheter would be connected to the defibrillation patch electrode in the manner discussed above.

Figure 4:
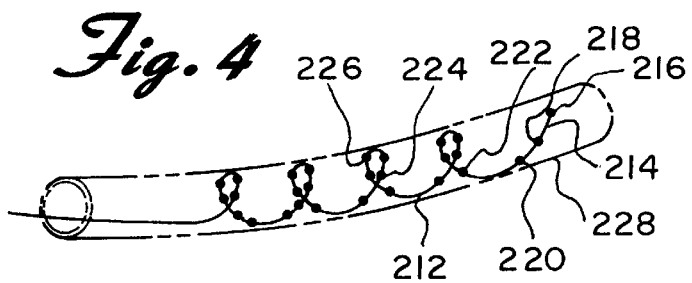
FIG. 4 is a perspective view of a second embodiment of the catheter where the catheter is placed within the coronary sinus.
Figure 2:
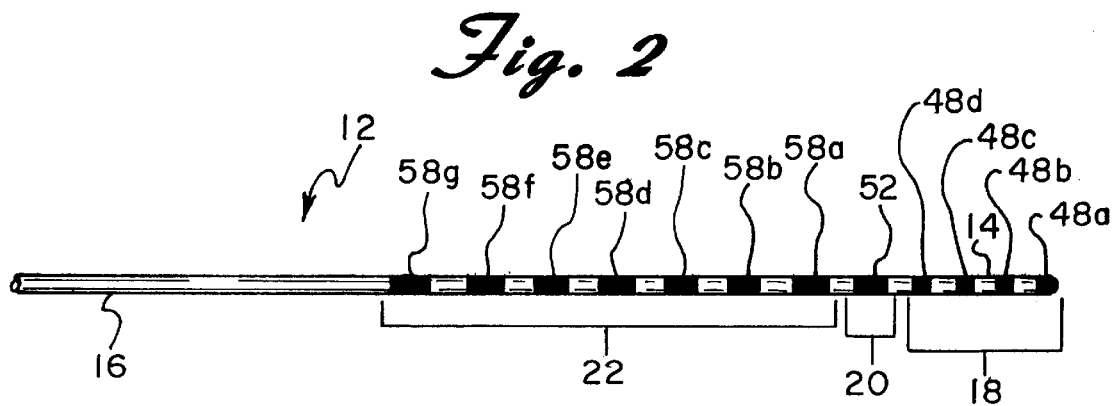
FIG. 2 is a partial perspective view of the catheter of the present invention.
Figure 5:
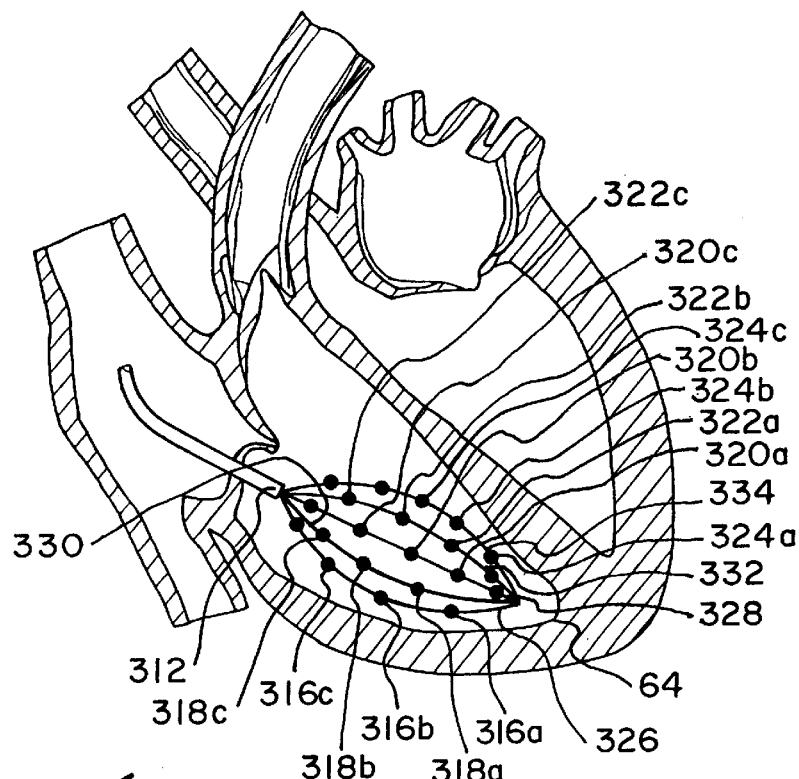
FIG. 5 is a perspective view of a third embodiment of the catheter where the catheter is placed within the ventricle.

The configuration of the catheter may take many forms. For example, one form is a fairly straight catheter 212 with a curve 214 on the distal end and surface electrodes 216, 218, 220, 222, 224, and 226, for example, located along the distal end of the catheter 212. Catheter 212 may be placed within the coronary sinus 228. (See FIG. 4.) Another configuration is a "basket" type catheter 312, wherein a number of electrodes 316*a*–*c*, 318*a*–*c*, 320*a*–*c*, 322*a*–*c*, and 324*a*–*c*, for example, are affixed to spines 326, 328, 330, 332, and 334, respectively, of the catheter 312. The spines 326, 328, 330, 332, and 334 form a circumferential or elliptical configuration much like a "basket" within the ventricle or atrium. (See FIG. 5.)

Figure 6:
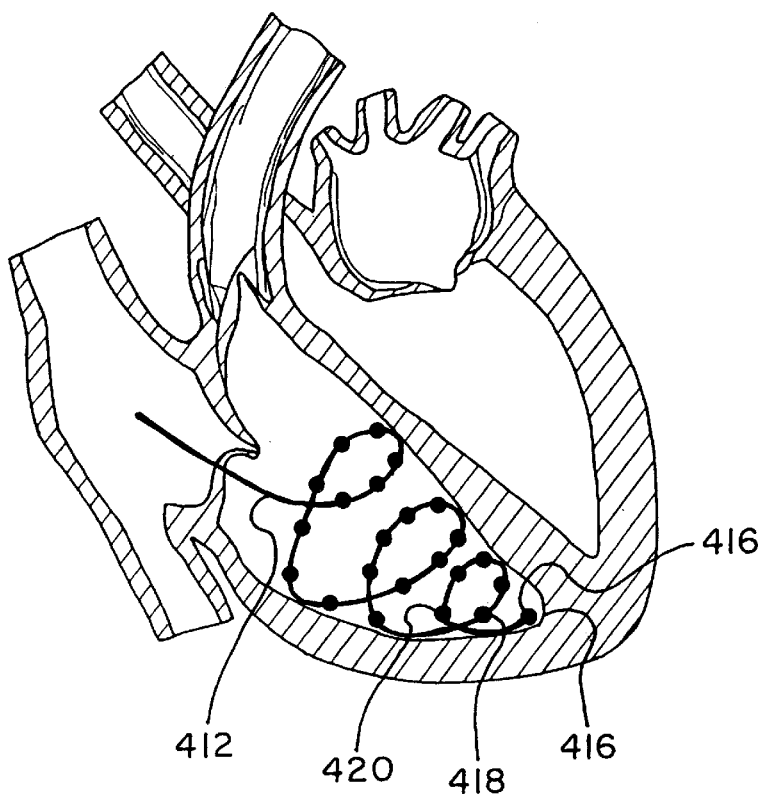
FIG. 6 is a perspective view of a fourth embodiment of the catheter where the catheter is placed within the ventricle.

Yet another configuration is an extremely flexible catheter 412 which may be pushed around the inside of the cavity so that the catheter 412 is formed into the shape of a helix or corkscrew again, with electrodes 416, 418, and 420, for example, on the surface of the distal end of the catheter 412. (See FIG. 6.) This formation may be aided by the use of one or more removable stylets (not shown) which would pass through a lumen (not shown) to assist in positioning the catheter 412. The formation of a helix or corkscrew type configuration may also be aided by one or more fixed stylets, where such fixed stylets are made of a memory alloy metal, such as nitinol and where such metal can take a pre-formed helical shape once the catheter is advanced to the cavital area of the heart.

Generally, the electrodes can be of different materials and configurations. The size of a single electrode can be from between approximately 1 mm and 5 mm, measured lengthwise down the shaft of the catheter. The electrodes may be hard bands wired to the catheter shaft. Alternatively, the electrodes may be manufactured onto the catheter by such techniques as sputtering or ion beam assisted deposition, as discussed above. These electrodes are preferable to the electrode bands because the catheter is more flexible along the entire catheter shaft where the electrodes are located as opposed to only being flexible in the area between the bands. Also, the material of the electrodes may be any conductive material, such as stainless steel, silver, gold, platinum, or a combination of different conductive materials.

Using any of the catheters described above with the present procedure less energy, for example 3 to 50 Joules, is required than the traditional procedure of using two external paddles, which may use 300 to 360 Joules and which traumatizes the patient to such an extent that the patient must recuperate before the testing may continue. Also, by using the catheter already in place, less time is required to start the defibrillation thereby decreasing any risk to the patient's life. This procedure is also minimally invasive and causes minimal, if any, side effects in the patient. Furthermore, testing may be continued once the patient's heart resumes its natural rhythm.

The present invention may be embodied in other specific forms without departing from the spirit or essential attributes thereof and accordingly, reference should be made to the appended claims rather than to the foregoing specification as indicating the scope of the invention.

We claim:

1. An electrophysiology catheter for defibrillating a patient's heart comprising:

an elongated flexible member with a distal end and a proximal end;

said distal end having a plurality of surface electrodes being arranged in a helical configuration;

an external patch electrode;

a manifold secured around said proximal end of said flexible member;

a plurality of cables extending proximally from said manifold; and means for connecting one of said cables to said external patch electrode.

2. The electrophysiology catheter for defibrillating a patient's heart claimed in claim 1 wherein each of said surface electrodes has a length between approximately 1 and approximately 5 millimeters.

3. The electrophysiology catheter for defibrillating a patient's heart claimed in claim 1 wherein each of said surface electrodes is flexible.

4. The electrophysiology catheter for defibrillating a patient's heart as claimed in claim 3 wherein said surface electrodes are formed on said flexible member by ion-beam assisted deposition of electrically conductive material.

5. An electrophysiology catheter for defibrillating a patient's heart comprising:

an elongated flexible member with a distal end and a proximal end;

said distal end having a plurality of spines and a plurality of surface electrodes arranged on each of said spines;

an external patch electrode;

a manifold secured around said proximal end of said flexible member;

a plurality of cables extending proximally from said manifold; and means for connecting one of said cables to said external patch electrode.

6. The electrophysiology catheter for defibrillating a patient's heart claimed in claim 5 wherein each of said surface electrodes has a length between approximately 1 and approximately 5 millimeters.

7. The electrophysiology catheter for defibrillating a patient's heart as claimed in claim 5 wherein said surface electrodes are formed on said spines by ion-beam assisted deposition of electrically conductive material.

* * * * *